(12) United States Patent
Meir et al.

(10) Patent No.: US 10,154,803 B2
(45) Date of Patent: Dec. 18, 2018

(54) PATIENT MONITOR

(71) Applicant: VISION RT LIMITED, London (GB)

(72) Inventors: Ivan Daniel Meir, London (GB);
Norman Ronald Smith, London (GB);
Anthony Christopher Ruto, London (GB)

(73) Assignee: VISION RT LIMITED, London (GB)

( * ) Notice: Subject to any disclaimer, the term of this patent is extended or adjusted under 35 U.S.C. 154(b) by 539 days.

(21) Appl. No.: 14/688,853

(22) Filed: Apr. 16, 2015

(65) Prior Publication Data

US 2015/0216450 A1 Aug. 6, 2015

Related U.S. Application Data

(60) Division of application No. 12/379,108, filed on Feb. 12, 2009, now Pat. No. 9,028,422, which is a
(Continued)

(30) Foreign Application Priority Data

Sep. 5, 2006 (GB) .................................. 0617472.6

(51) Int. Cl.
*A61B 5/113* (2006.01)
*G06T 7/593* (2017.01)
(Continued)

(52) U.S. Cl.
CPC ............ *A61B 5/113* (2013.01); *A61B 5/0077* (2013.01); *A61B 5/7285* (2013.01); *A61B 6/541* (2013.01);
(Continued)

(58) Field of Classification Search
CPC ..... A61B 5/113; A61B 5/0077; A61B 5/7285; A61B 6/541; A61B 2576/02; G06T 7/593;
(Continued)

(56) References Cited

U.S. PATENT DOCUMENTS 5,931,779 A * 8/1999 Arakaki ............... A61B 5/1459
600/310
6,621,889 B1 9/2003 Mostafavi
(Continued)

FOREIGN PATENT DOCUMENTS

EP 1640922 A2 3/2006
GB 2371964 A 8/2002
(Continued)

OTHER PUBLICATIONS

Frangi et al., Automatic Construction of Multiple-Object Three-Dimensional Statistical Shape Models: Application to Cardiac.
(Continued)

*Primary Examiner* — Navin Natnithithadha
(74) *Attorney, Agent, or Firm* — Birch, Stewart, Kolasch & Birch, LLP

(57) ABSTRACT

A patient monitor is disclosed for detecting patient movement or abnormal breathing. Images of a patient are obtained by a stereoscopic camera. These images are then processed by a 3D position determination module which determines measurements indicative of positions of at least part of a patient. The obtained measurements are then passed to a model generation module which generates a breathing model of the variation in position of the at least part of a patient during a breathing cycle. Subsequently abnormal breathing or patient movement can be detected by processing further images obtained by the stereoscopic camera to determine more measurements indicative of positions of at least part of a patient. These measurements are then compared with a stored breathing model by a comparison module. If abnormal breathing or patient movement is detected the comparison module sends a signal to a treatment apparatus to interrupt treatment until normal breathing resumes or alternatively to a mechanical couch to reposition the patient to account for the detected movement.

3 Claims, 9 Drawing Sheets

Related U.S. Application Data continuation-in-part of application No. PCT/GB2007/003333, filed on Sep. 5, 2007.

(51) Int. Cl.
  *A61B 5/08* (2006.01)
  *A61B 6/00* (2006.01)
  *A61N 5/10* (2006.01)
  *A61B 5/00* (2006.01)

(52) U.S. Cl.
  CPC ............ *A61N 5/1049* (2013.01); *G06T 7/593* (2017.01); *A61B 2576/02* (2013.01); *A61N 5/1064* (2013.01); *A61N 2005/1059* (2013.01); *G06T 2207/10021* (2013.01); *G06T 2207/10076* (2013.01); *G06T 2207/10081* (2013.01); *G06T 2207/30096* (2013.01)

(58) Field of Classification Search
  CPC . G06T 2207/10021; G06T 2207/10076; G06T 2207/10081; G06T 2207/30096; A61N 5/1049; A61N 5/1064; A61N 2005/1059
  USPC .................. 600/529, 533–536, 538, 547
  See application file for complete search history.

(56) References Cited

U.S. PATENT DOCUMENTS

| | | | |
|---|---|---|---|
| 6,937,696 B1 * | 8/2005 | Mostafavi | A61B 5/113 378/65 |
| 6,959,266 B1 * | 10/2005 | Mostafavi | A61B 6/541 378/64 |
| 6,980,679 B2 | 12/2005 | Jeung et al. | |
| 7,123,758 B2 | 10/2006 | Jeung et al. | |
| 7,343,197 B2 * | 3/2008 | Shusterman | A61B 5/0452 600/509 |
| 7,485,095 B2 * | 2/2009 | Shusterman | A61B 5/04007 600/508 |
| 7,801,591 B1 * | 9/2010 | Shusterman | A61B 5/0205 600/300 |
| 8,388,530 B2 * | 3/2013 | Shusterman | G06F 19/3443 600/300 |
| 8,749,626 B2 * | 6/2014 | Ishii | A61B 5/1113 348/77 |
| 9,028,422 B2 * | 5/2015 | Meir | A61B 5/113 600/534 |
| 9,183,351 B2 * | 11/2015 | Shusterman | G06F 19/3443 |
| 9,224,202 B2 * | 12/2015 | De Haan | G06T 7/0016 |
| 9,456,947 B2 * | 10/2016 | Dawson | A61G 13/121 |
| 9,486,647 B2 * | 11/2016 | Bergfjord | A61N 5/1048 |
| 9,731,150 B2 * | 8/2017 | Hale | G06T 15/04 |
| 2004/0193064 A1 | 9/2004 | Shusterman | |
| 2006/0074304 A1 | 4/2006 | Sayeh | |
| 2006/0079757 A1 | 4/2006 | Smith et al. | |
| 2006/0122525 A1 * | 6/2006 | Shusterman | A61B 5/04007 600/513 |
| 2007/0231779 A1 | 10/2007 | Santhanam et al. | |

FOREIGN PATENT DOCUMENTS

| | | |
|---|---|---|
| WO | 03003796 A1 | 1/2003 |
| WO | WO2004004828 A2 | 1/2004 |
| WO | 2005032647 A2 | 4/2005 |
| WO | 2006/113323 A2 | 10/2006 |

OTHER PUBLICATIONS

Modeling, IEEE Transactions on Medical Imaging, vol. 21, No. 9, Sep. 2002, pp. 1151-1166.
Velastin & Xu. "Line and circle finding by the weighted Mahalanobis distance transform and extended Kalman filtering" IEEE International Symposium on Industrial Electronics, 1994. Symposium Proceedings, ISIE '94. May 25-27, 1994, pp. 258-263.

* cited by examiner

PATIENT MONITOR

RELATED APPLICATION

This application is a Divisional Application of U.S. patent application Ser. No. 12/379,108 filed Feb. 12, 2009, which is a continuation in part of PCT/GB2007/003333 filed Sep. 5, 2000, which claim the priority benefit under 35 U.S.C. § 119 of British Patent Application No. 0617472.6, filed on Sep. 5, 2006, all of which are hereby incorporated in their entireties by reference.

FIELD OF THE INVENTION

The present invention relates to patient monitoring. More particularly, embodiments of the present invention relate to modelling breathing in order to detect breathing abnormalities (e.g. coughing) and also to enable the movement of patients to be detected. The invention is particularly suitable for use with radio therapy devices and computed tomography (CT) scanners and the like where detection of patient movement or irregular breathing is important for successful treatment.

BACKGROUND TO THE INVENTION

Radiotherapy consists of projecting onto a predetermined region of a patient's body, a radiation beam so as to destroy or eliminate tumours existing therein. Such treatment is usually carried out periodically and repeatedly. At each medical intervention, the radiation source must be positioned with respect to the patient in order to irradiate the selected region with the highest possible accuracy to avoid radiating adjacent tissue on which radiation beams would be harmful.

When a tumour is located in the thoracic or abdominal chest cavities, the position of a tumour can vary considerably (e.g. by as much as a few centimeters) throughout the breathing cycle. In order to obtain reliable CT scanning data it is therefore important to obtain data consistently at the same point within a breathing cycle.

Certain modern CT scanners are able to process CT scanning data acquired at different times within a breathing cycle to generate a representation of the 3D movement of internal organs during breathing. Such "4D" representations of organ movement are invaluable in determining a course of treatment for irradiating a cancer. Again in order for quality planning data to be generated, the timing within the breathing cycle when individual CT scans are acquired must be known so that 4D representation accurately represents the movement of the internal organs.

When applying radiation to a patient, the gating of treatment apparatus should be matched with the breathing cycle so that radiation is focused on the location of a tumour and collateral damage to other tissues is minimised. If movement of a patient is detected the treatment should be halted to avoid irradiating areas of a patient other than a tumour location. Also if irregular breathing such as coughing is detected, treatment should be halted as such irregular breathing may cause a tumour to change location relative to the focus of a radiation beam.

For this reason a number of monitoring systems for monitoring a patient's breathing during radiotherapy have therefore been proposed. Thus for example, U.S. Pat. No. 6,621,889 discloses a system in which the gating of a radiation apparatus is linked to a determination that the periodicity of a patients breathing has deviated from an earlier measurement. Further examples are U.S. Pat. No. 6,980,679 and U.S. Pat. No. 7,123,758 which disclose a system for monitoring breathing of infants and reporting irregularities based on the periodicity of a patients breathing deviating from an earlier measurement.

An improved system for monitoring and measuring patient breathing and movement is, however desirable.

SUMMARY OF THE INVENTION

In accordance with one aspect of the present invention there is provided a method of monitoring a patient comprising: obtaining data representative of a measurement indicative of the timing and position of at least part of a patient during at least one breathing cycle; using the obtained data to generate a model of the variation in position of the at least part of a patient during the at least one breathing cycle, said model being responsive to receipt of input data indicative of position and timing to determine a set of weights for modelling a representation of said input data; obtaining further data representative of a measurement indicative of the timing and position of the at least part of a patient during a subsequent period of breathing; determining a set of weights for modelling a representation of said further data utilising said generated model; calculating a plausibility measure indicative of the probability of said representation of said further obtained data arising based on the set of weights determined for modelling said representation; and comparing said plausibility measure of with a threshold value.

In accordance with another aspect of the present invention there is provided a patient monitor comprising: a 3D position determination module operable to determine measurements indicative of positions of at least part of a patient; a clock module operable to associate measurements indicative of positions of at least part of a patient determined by said 3D position determination module with timing data, a model generation module operable to use the obtained position and timing data to generate a model of the variation in position of the at least part of a patient during the at least one breathing cycle, said model being responsive to receipt of input data indicative of position and timing to determine a set of weights for modelling a representation of said input data; and a comparison module operable to calculate a plausibility measure indicative of the probability of a representation arising based on the set of weights determined for modelling said representation and compare said plausibility measure of with a threshold value.

In accordance with further aspect of the present invention there is provided a method of monitoring a patient comprising: obtaining images of a patient during at least one breathing cycle; processing obtained images to generate a model of the variation of at least part of the surface of the patient during a breathing cycle; obtaining a further image of the patient during a subsequent period of breathing and processing the image to generate a 3D wire mesh model of the surface of the at least part of a patient appearing in the further image; comparing the generated 3D wire mesh model of the surface of the at least part of a patient appearing in an obtained image with a modelled representation of the surface generated utilising said model of the variation of at least part of the surface of the patient during a breathing cycle; and determining a transformation required to match the 3D wire mesh model with the modelled representation.

In accordance with another aspect of the present invention there is provided a patient monitor comprising: a 3D position determination module operable to process obtained images of a patient during at least one breathing cycle to determine the a 3-D wire mesh model of at least part of the surface of a patient appearing in the images; a clock module operable to 3-D wire mesh models generated by the 3D position determination module with timing data; a model generation module operable to use the generated 3-D wire mesh models and timing data to generate a linear model of the variation of the surface the at least part of a patient during the at least one breathing cycle, said model being responsive to receipt of input data indicative of a surface and timing to determine a set of weights for modelling a representation of said surface; and a comparison module operable to compare a generated 3D wire mesh model of the surface of the at least part of a patient appearing in an obtained image with a modelled representation of the surface generated utilising said model of the variation of at least part of the surface of the patient during a breathing cycle; and determine a transformation required to match the 3D wire mesh model with the modelled representation.

In accordance with a further aspect of the present invention there is provides a method of monitoring a patient comprising: obtaining data indicative the timing and position of at least part of a patient during at least one breathing cycle; partitioning the obtained data into a plurality of groups of data each associated with different portions of the breathing cycle; using the partitioned data to generate a plurality of models of the variation in position of the at least part of a patient during the respective different portions of the breathing cycle; obtaining further data representative of measurement indicative of position of the at least part of a patient during a subsequent period of breathing; and detecting breathing which does not correspond to the initial obtained data using the plurality of models and the further obtained data.

In accordance with another aspect of the present invention there is provided a patient monitor comprising: a 3D position determination module operable to determine measurements indicative of positions of at least part of a patient; a clock module operable to associate measurements indicative of positions of at least part of a patient determined by the 3D position determination module with timing data, a model generation module operable to partition the position and timing data into a plurality of groups of data each associated with different portions of the breathing cycle and utilise the portioned data to generate a plurality of models of the variation in position of the at least part of a patient during the respective different portions of the breathing cycle; and a comparison module operable to utilise position and timing data and a plurality of models generated by the model generation module to identify breathing which differs from that occurring in the images used to generate the models.

BRIEF DESCRIPTION OF THE DRAWINGS

Embodiments of the present invention will now be described with reference to the accompanying drawings in which.

DETAILED DESCRIPTION OF THE PREFERRED EMBODIMENTS

First Embodiment

Figure 1:
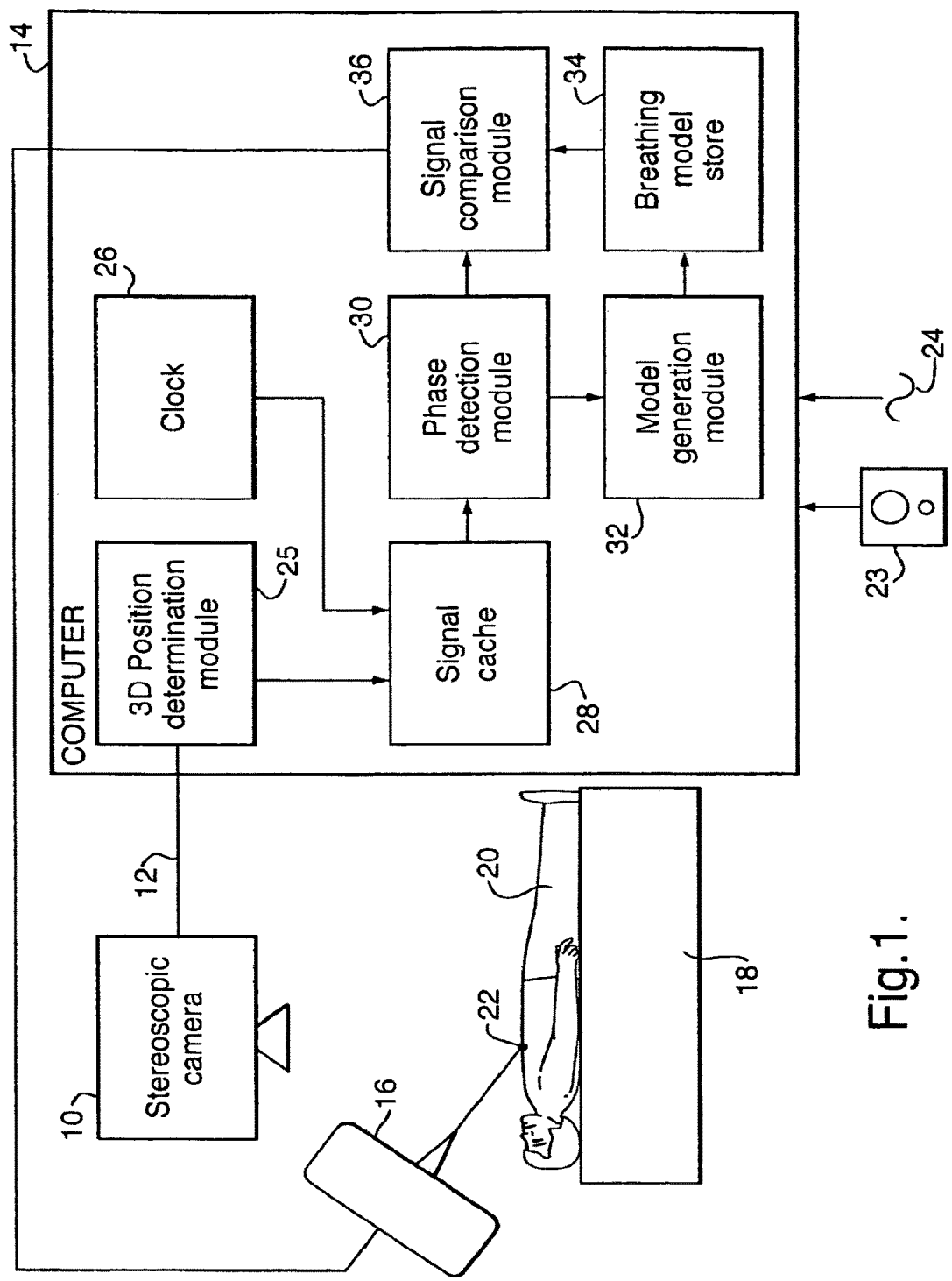
FIG. 1 is a schematic diagram of a patient monitor in accordance with a first embodiment of the present invention.

FIG. 1 is a schematic diagram of a patient monitor in accordance with a first embodiment of the present invention. In accordance with this embodiment, there is provided a stereoscopic camera 10 that is connected by wiring 12 to a computer 14. The computer 14 is also connected to treatment apparatus 16 such as a linear accelerator for applying radiotherapy or an x-ray simulator for planning radiotherapy. A mechanical couch 18 is provided as part of the treatment apparatus upon which a patient 20 lies during treatment. The treatment apparatus 16 and the mechanical couch 18 are arranged such that under the control of the computer 14 the relative positions of the mechanical couch 18 and the treatment apparatus 16 may be varied, laterally, vertically, longitudinally and rotationally. Provided on the surface of the patient 20 is a marker 22.

In use, the cameras of the stereoscopic camera 10 obtain video images of a patient 20 lying on the mechanical couch 18. These video images are passed via the wiring 12 to the computer 14. The computer 14 then processes the images of the marker 22 on the patient 20 to generate a model of the patient's breathing. Subsequently the patient's breathing is monitored and compared with the stored model and if abnormal breathing is detected, the treatment apparatus 16 is shut off until normal breathing resumes.

In order for the computer 14 to process images received from the stereoscopic camera 10, the computer 14 is configured by software either provided on a disk 23 or by receiving an electrical signal 24 via a communications network into a number of functional modules 25-36. It will be appreciated that the functional modules 25-36 illustrated in FIG. 1 are purely notional in order to assist with the understanding of the working of the claimed invention and may not in certain embodiments directly correspond with blocks of code in the source code for the software. In other embodiments the functions performed by the illustrated functional modules 25-36 may be divided between different modules or may be performed by the re-use of the same modules for different functions.

In this embodiment, the functional modules 25-36 comprise: a 3D position determination module 25 for processing images received from the stereoscopic camera and determining a breathing signal on the basis of a detected 3D position for the marker 22; a clock module 26 for providing a timestamp for portions of breathing signals determined by the 3D position determination module 25; a signal cache for storing time stamped breathing signals; a phase detection module 30 for processing the signals stored in the signal cache to divide the signals into individual breathing cycles; a model generation module 32 and breathing model store 34 for generating and storing a principal component analysis breathing model; and a signal comparison module 36 for comparing received breathing signals with a stored breathing model to identify abnormal breathing.

In use, as images are obtained by the stereoscopic camera 10, these images are processed by the 3D position determination module 25 which determines the 3D position for the position of the marker 22. The 3D position determination module 25 then converts this 3D position signal into a distance measure indicating the relative distance of the marker 22 from a fixed reference point. This distance data is then stored in the signal cache 28 together with timing data indicating the timing at which the image of the marker 22 was obtained.

During a training phase, after distance and timing data for a number of breathing cycles has been stored in the signal cache 28, this data is passed to the phase detection module 30 which divides the stored data into a number of sections where each section corresponds to an individual breathing cycle. Data representing these individual breathing cycles is then passed to the model generation module 32 which proceeds to generate a principal component analysis model of the usual variation of the patient's breathing which is stored in the breathing model store 34.

In contrast during a monitoring phase, the phase detection module 30 monitors the data stored in the signal cache 28 and as soon as data corresponding to a complete breathing cycle has been stored, the phase detection module passes the data to the signal comparison module 36 which compares the signal with the principal component analysis breathing model stored in the breathing model store 34.

Due to the manner in which the principal component analysis breathing model stored in the breathing model store 34 is generated, the model will identify whether the latest detected breathing cycle corresponds to a breathing cycle within the usual variation of normal breathing for the patient 20. If the stored principal component analysis breathing model is unable to model the latest detected breathing cycle, this indicates that the patient's breathing is abnormal. In this embodiment, if the signal comparison module 36 detects two consecutive abnormal breathing cycles, the signal comparison module 36 sends a signal to the treatment apparatus 16 to interrupt treatment until two consecutive normal breathing cycles are detected. In this way in the event that the patient 20 begins coughing during treatment, the treatment is halted until the patient begins breathing normally once again.

Generation of a Breathing Model

The processing performed by the patient monitor of FIG. 1 to generate a breathing model for detecting irregular breathing will now be described in detail with reference to FIGS. 2-5.

Figure 2:
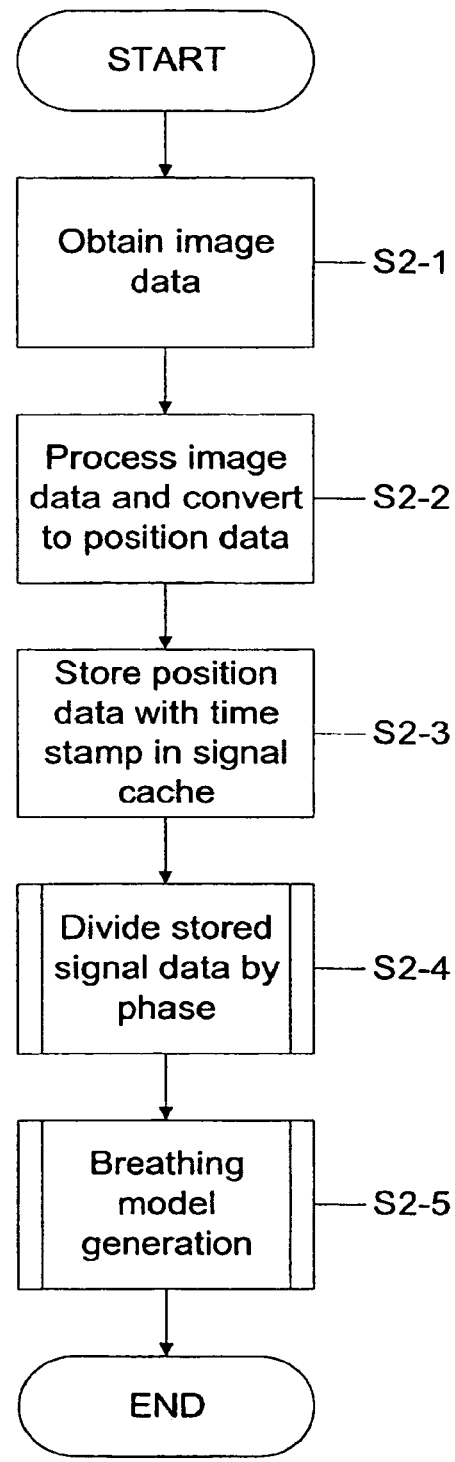
FIG. 2 is a flow diagram of the processing the processing undertaken by the patient monitor of FIG. 1 to generate a breathing model for detecting irregular breathing.

Referring to FIG. 2 is a flow diagram of the processing undertaken by the processing patient monitor of FIG. 1, when a breathing model is to be generated, initially (S2-1), the stereoscopic camera 10 captures images of marker 22 on the patient 20.

These images are then passed to the 3D position determination module 25 which processes (S2-2) the obtained stereoscopic images to identify the location of the marker 22 in the images. The location of the marker 22 in a pair of images is then processed together with stored data regarding the relative location of the cameras in the stereoscopic camera in a conventional way to convert the differences in position of a marker in a pair of captured images into an instantaneous measurement of the 3D location of the marker 22.

The 3D position determination module 25 then compares this 3D location with a reference location and calculates the distance between the two. In this embodiment, the reference location corresponds to a reference position somewhere within the chest cavity of the patient 20. The 3D position determination module 25 then passes the calculated distance measurement to the signal cache 28 where it is stored (S2-3) together with a timestamp obtained from the clock 26 indicating the time at which the images used to generate the distance measure where obtained by the stereoscopic camera 10.

Figure 3A:
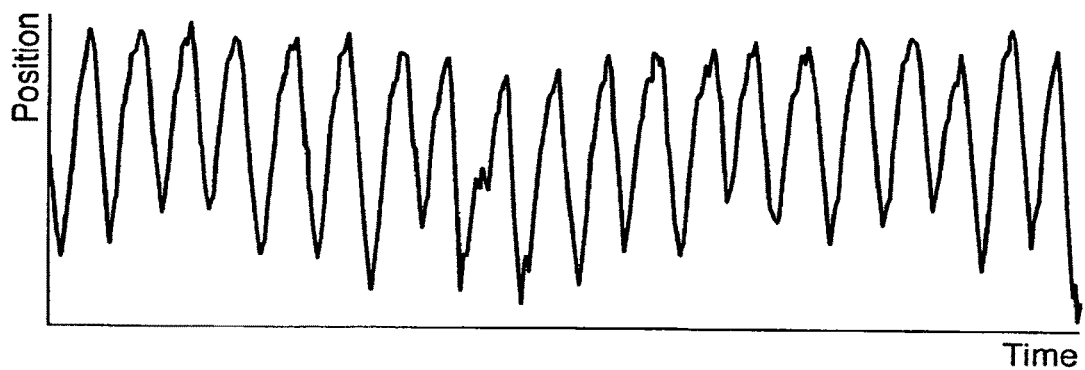
FIGS. 3A-B are a diagram of an example of a breathing signal and a sectioned breathing signal generated by the patient monitor of FIG. 1.

FIG. 3A is an exemplary illustration of a plot of timing and position data for a period of monitored breathing such as may be stored by the 3D position determination module 25 in the signal cache. It will be noted that although the signal is approximately periodic, a typical signal will vary both due to the relative extent of inhale and exhale for an individual breathing cycle and the duration of individual breathing cycles. Further the overall shape of data for breathing cycles will vary as a patient takes individual breaths in slightly different ways. Due to this natural variation in breathing, simple detectors based on detecting variations in the periodicity of breathing can be unsatisfactory as variations in periodicity can arise even when breathing is relatively regular.

When position and timing data for a number of breathing cycles such as is illustrated in FIG. 3A has been stored within the signal cache 28, the phase detection module 30 then proceeds to process (S2-4) the stored signal data to divide the signal data into a number of sections where each section corresponds to an individual breathing cycle so that a breathing model of the normal variations of breathing as exemplified by the stored signal can be generated (S2-5).

Figure 3B:
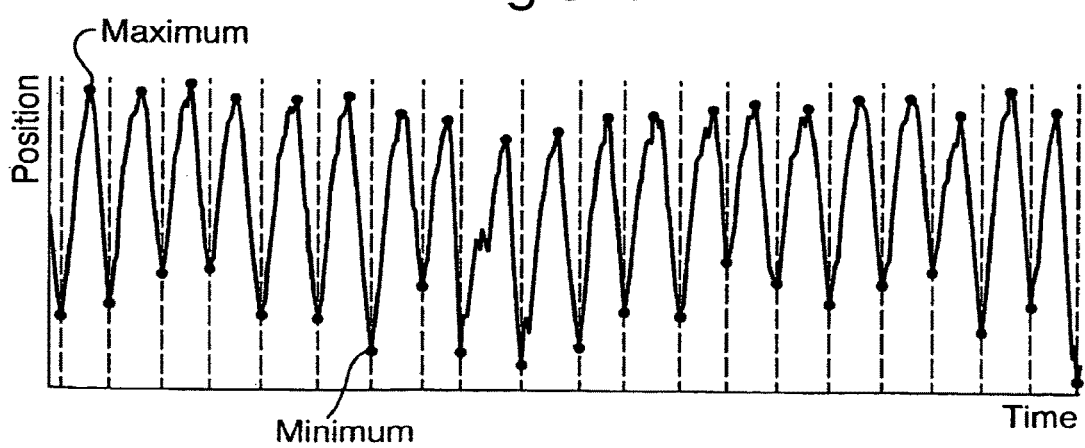

The processing undertaken by the phase detection module 30 to divide a stored breathing signal into sections corresponding to individual breathing cycles such as is illustrated in FIG. 3B will now be described in detail with reference to FIG. 4.

Phase Detection

Figure 4:
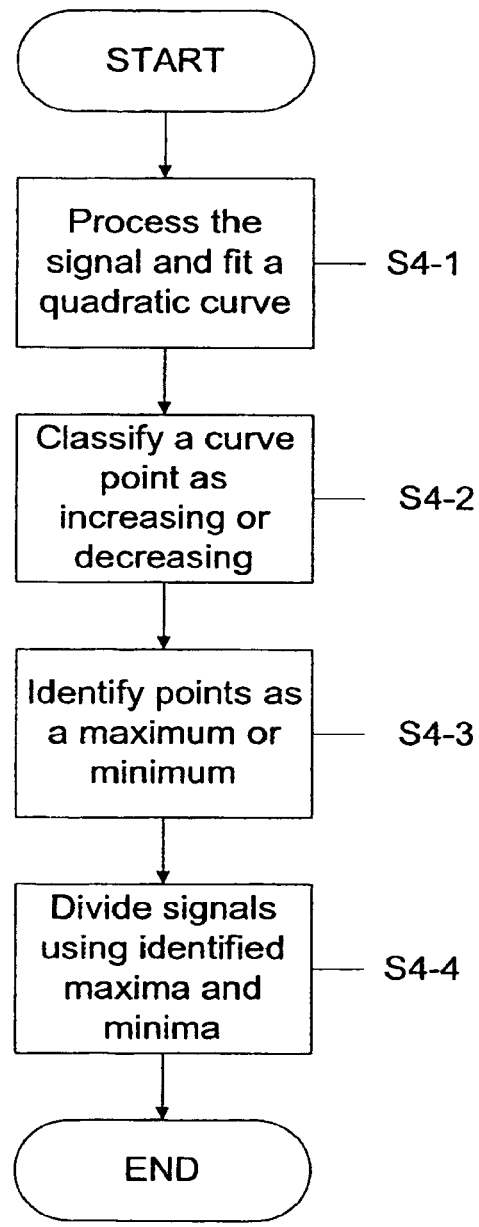
FIG. 4 is a flow diagram of the processing involved in dividing a breathing signal into a number of sections.

Referring to FIG. 4 which is a flow diagram of the processing involved in dividing a breathing signal into a number of sections, once position and timing data for a number of breathing cycles have been stored in the signal cache 28, the phase detection module 30 divides the signal into section representing individual breathing cycles by processing the stored signal to identify points corresponding to the middle and beginning/end of each breathing cycle. These points can be identified by determining the maximum and minimum position values associated with a breathing cycle which will correspond to points of maximum inhale and exhale respectively.

Due to the variability of the extent of inhale and exhale between different breathing cycles, this identification cannot be reliably achieved directly through the value of a position measurement itself. The maxima and minima can, however, be identified by identifying the turning points in the signal. In order to do so, it is, however, necessary to be able to distinguish between true maxima and minima and local maxima and minima which can arise due to noise or general irregularity in breathing.

To this end in order to identify points in a breathing signal corresponding to maximum inhale and the end of exhale, initially (S4-1) the signal is matched to a quadratic curve. In this embodiment, the signal is matched to a Legendre quadratic, which is a quadratic curve defined on the interval [−1, 1] and having the form $A0 + xA1 + (x^2 − 1/3) A2$. In the case of such a curve the three basis functions $\{1, x, x^2 − 1/3\}$ have the property that they are orthogonal with respect to integration over this interval. In general however these basis functions will not be orthogonal when using a discrete version of the integration, for example a sum defined over the corresponding range. In this case, a correction needs to be computed for each new set of sampling x values, yielding a curve of the form $A0 + xA1 + (x^2 − t) A2$, where t is the correction to be estimated and the three basis functions $\{1, x, x^2 − t\}$ are orthogonal with respect to the sum chosen.

The fitting to signal data (x1, y1) can be achieved using the standard technique of solving an over-determined system of equations $A0 + xi \, A1 + (xi^2 − t) \, A2 = yi$ for the coefficients A0, A1 and A2, noting that the orthogonality of $\{1, x, x^2 − t\}$ means that the system will be very well conditioned and hence resistant to noise and round-off errors Once the breathing signal has been matched with a suitable Legendre quadratic all the stored data points for a breathing signal can then be classified (S4-2) based on the behaviour of the matched quadratic. More specifically, each of the stored items of position and timing data in the signal cache 28 can be classified as either increasing if:

a) the corresponding curve is increasing over a range centred the point being considered;
b) the corresponding curve has a maximum over the range centred on the point being considered which lies to the right of the centre of the range; or
c) the corresponding curve has a minimum over the range centred on the point being considered which lies to the left of the centre of the range.

The remaining points are then classified as decreasing.

Signals corresponding to maxima and minima can then be identified (S4-3) using these classifications. In the case of a stored signal, this can be achieved by considering the classifications of sequences of point and identifying the points identified with a change of classification. Maxima can then be identified as those points where classification changes increasing to decreasing and minima identified where classifications change from decreasing to increasing. Alternatively, potential maxima and minima can be identified merely through a change in classification compared with immediately preceding points. Such an alternative system would be particularly suitable for classification of points in real time where signals are processed as soon as they are stored in the signal cache. In order to avoid detection of mere local maxima and minima the detection of maxima and minima can be limited to points where a change in classification occurs and at least three consecutive points following a detected maxima or minima maintain the same classifications.

Having processed the breathing signal data in this way, the breathing signal data can be divided (S4-4) into data corresponding to a series of breathing cycles by dividing the signals where ever a minimum signal is detected. The result of such a division of the data is illustrated in FIG. 3B. The division of a breathing signal representing normal breathing in this way provides data representing a series of exemplary breathing cycles which is then utilised to generate (S2-5) a breathing model as will now be described in detail.

Generation of a Principal Component Analysis Breathing Model

Figure 5:
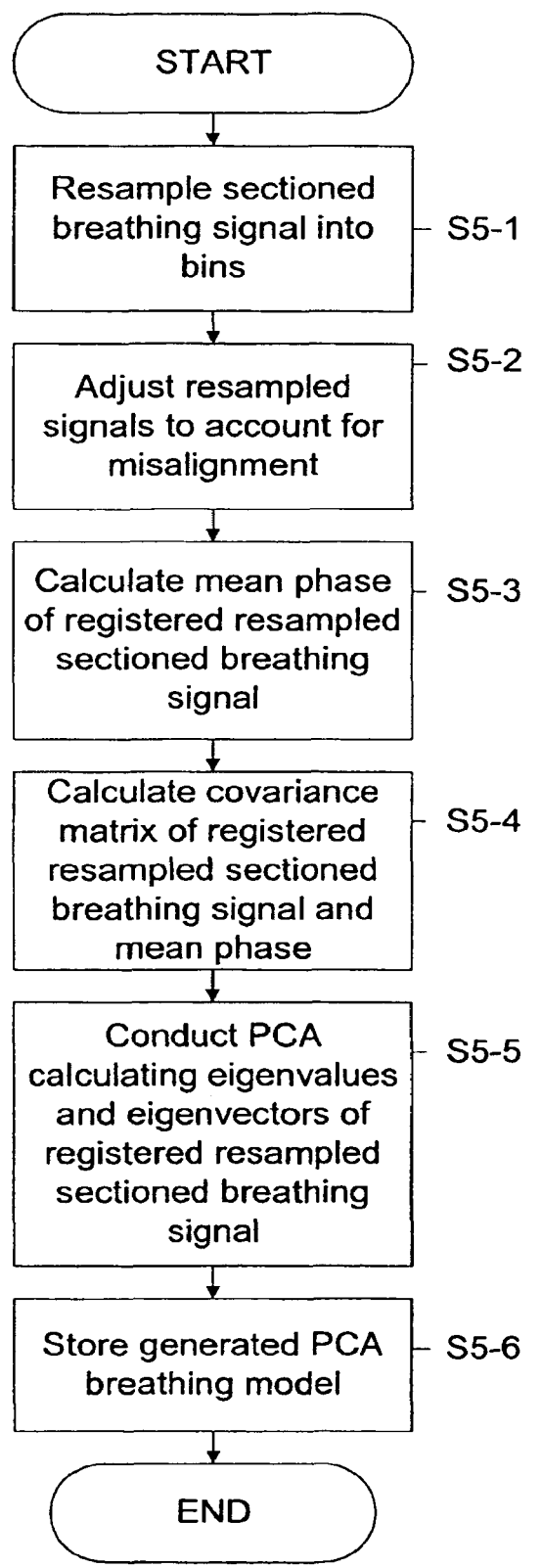
FIG. 5 is a flow diagram of the processing of a sectioned breathing signal to generate a breathing model.

Turning to FIG. 5 which is a flow diagram of the processing of a sectioned breathing signal to generate a breathing model, when the phase detection module 30 has sectioned a breathing signal into a series of samples each corresponding to a single breathing cycle each sample is processed in turn by the model generation module 32. The absolute timing data stored in the signal cache 28 is first converted into a set of relative timing measurements by subtracting the least timing data associated with a particular breathing cycle from all of the items of timing data for that cycle.

The identified sections in a breathing signal normally contain sections of varying lengths (periods) and as a result contain different numbers of data points. So that a suitable model can be generated, each of the sectioned signals is then resampled (S5-1) into a series of bins each associated with a portion of a complete breathing cycle.

In order to achieve this, first of all a suitable bin size is selected. In this embodiment, this is selected by considering the average number of data points associated with each of the breathing cycles for which data has been stored. For any particular breathing signal each of the stored items of position and timing data is the associated with a particular bin based on the relative position of the item of data within the breathing cycle. Thus for in the case of a breathing sample being re-sampled into 100 bins, the timing and position data associated with the start of a breathing cycle will be associated with the first bin and timing and position data associated with the end of the breathing cycle will be associated with the final bin with the remaining items of position and timing data being associated with intermediate bins depending upon their relative timing relative to the detected start and end of the breathing cycle. In the event that for a particular signal, no data is allocated to a particular bin, suitable timing and position data for a bin is generated by interpolating timing and position data using the data for adjacent timings. Conversely, if for a particular part of a breathing cycle multiple items of position and timing data are assigned to the same bin, an average of the timing and position values associated with a bin is determined and stored for that bin. The result of this processing is that for each of the detected breathing cycle, a resampled set of data will exist where the number of pairs of timing position of data for each breathing sample is the same.

The resampled signals are then adjusted (S5-2) to account for any differences between start, peak and end amplitudes. In an ideal setting, all sectioned breathing signals would have similar start, peak and end amplitudes as part of their inhale and exhale phase but this is not the case in practice. The variation in amplitude range is also independent of the actual shape of a sectioned breathing signal. Therefore in order to reduce any adverse effects in modelling the shape of a sectioned breathing signal, it is important to reduce any misalignment that may be present in a training sample.

In this embodiment, this is achieved by identifying as misaligned sectioned breathing signals, any signals whose inhale and exhale sequence lies in a different amplitude range to another. The position data associated with such misaligned signals is then amended to remove this difference. This is achieved by centring the mean amplitude (centroid) of all sections of a sectioned breathing signal, with the first in the sample as a reference. This is equivalent to carrying a least squares minimisation of the amplitude ranges of all sections in a sample relative to a reference section. This registration of the resampled sectioned breathing signals then makes it possible to calculate a mean sectioned breathing signal that accurately reflects the mean shape of the sectioned breathing signals in a sequence.

Having adjusted the position data to account for any variation in the extent of inhale or exhale in a particular cycle, the sample mean sectioned breathing signal $\bar{X}$ is then calculated (S5-3) using the registered and resampled sectioned breathing signals $X_i$. This is achieved by summing all sectioned breathing signal amplitudes and periods, and dividing these by the sample size. This is expressed as:

$$\bar{X} = \frac{1}{N}\sum_{i=1}^{N} X_i$$

where each $X_i$ is a vector of length M with sectioned breathing signal amplitudes and a period value, and N is the sample size.

A sample covariance matrix S is then calculated (S5-4) using all $X_i$ (columns of a M×N matrix X) and $\bar{X}$ prior to using principal component analysis to calculate principal or significant variations in sectioned breathing signal shape that may be present in the sample used. S is therefore calculated as:

$$S=(X-\bar{X})(X-\bar{X})^T$$

Principal component analysis is then (S5-5) used to capture principal or significant variations present in the registered and resampled sectioned breathing signal sample data. These variations indicate the different ways in which the different sectioned breathing signals present in the sample varied from the mean shape. Principal component analysis therefore identifies principal variations j as a set of eigenvectors $P_j$ (directions of variation) and eigen values $\lambda_j$ (variances corresponding to the eigenvectors) through carrying out an eigen decomposition of the sample covariance matrix S. The principal variations are then ordered in a descending order based on the eigen values $\lambda_j$. The directions $P_j$ which have the most significant variations can then be identified. These significant variations will be the variations indicating variations in shape and period which contribute the most to the variations in the observed sectioned breathing signals stored in the signal cache 28.

Finally, a principal component analysis model for the sample breathing signal stored in the signal cache 28 is then stored (S5-6) in the breathing model store 34 by storing data identifying the sample mean $\bar{X}$ and the principal variations $P_j$ and $\lambda_j$ calculated using principal component analysis. This stored model therefore defines a linear generative model where sectioned breathing signal Y can be generated as:

$$Y = \bar{X} + \sum_{j=1}^{T} w_j \sqrt{\lambda_i}\, P_j$$

where all $w_j$ are weights used to vary the contributions of the different principal variations, and T is the number of principal variations used in the model.

In this embodiment the weights $w_j$ are given a value of ±2 when individual principal variations j are displayed, while T is chosen as the number of variations that capture 90-100% of the sample variance, as calculated from the ordered $\lambda_j$.

This linear generative model also makes it possible to fit a sectioned breathing signal PCA model to newly captured sectioned breathing signal data as discussed in the following section.

Comparison of Live Data with Breathing Model

The use of a generated breathing model to identify periods of abnormal breathing will now be described with reference to FIGS. 6 and 7.

Figure 6:
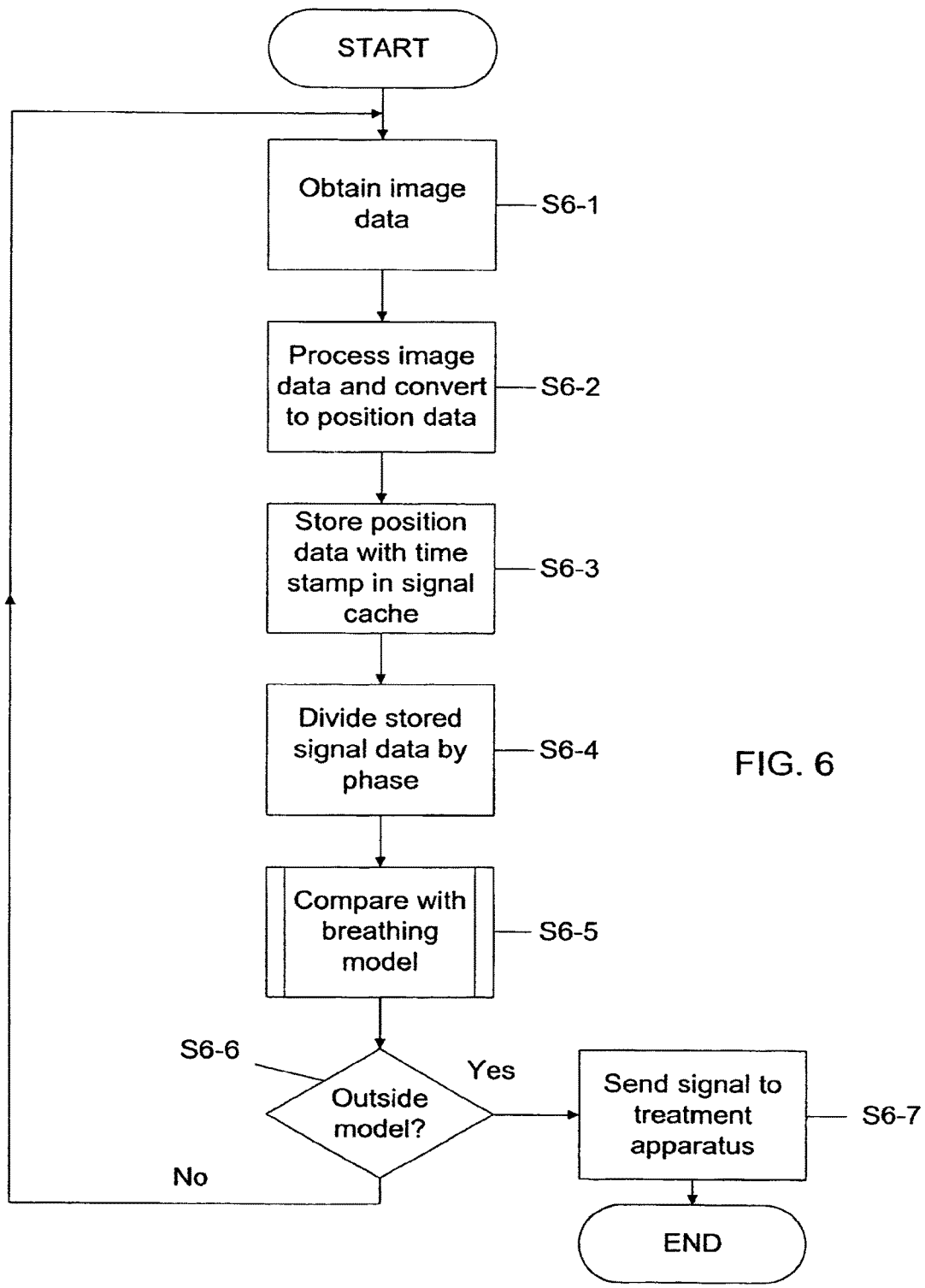
FIG. 6 is a flow diagram of the processing undertaken by the patient monitor of FIG. 1 to identify a period of irregular breathing using a generated breathing model.

Referring to FIG. 6 is a flow diagram of the processing undertaken by the patient monitor to identify a period of irregular breathing using a generated breathing model, the initial processing of undertaken by the patient monitor is essentially identical to that undertaken when obtaining an initial training sample to generate a breathing model. As described in relation to the generation of a breathing model, initially image data is obtained (S6-1) by the stereoscopic camera 10 and processed to determine (S6-2) position data for the position of a marker 22 present on the surface of a patient 20. This position data is then stored (S6-3) together with a time stamp in the signal cache 28.

The phase detection module 30 then processes (S6-4) the data stored in the signal cache 28 to identify the beginning and end points of a breathing cycle. This is achieved in the manner previously described in relation to identifying the start and end points of a breathing cycle in a stored signal when a breathing model is being generated. When the phase detection module 30 identifies that data for a complete breathing cycle has been stored in the signal cache 28, the stored signal is then passed to the signal comparison module 36 which analyses (S6-5) the signal by comparing the signal with the stored breathing model. If the result of the analysis performed by the signal comparison module 36 determines (S6-6) that two successive signals cannot be modelled by the breathing model stored in the breathing model store 34, the signal comparison module 34 sends (S6-7) a signal to the treatment apparatus 16 to halt treatment until normal breathing is resumed and two successive breathing cycles which can be modelled by the breathing model have been detected.

The fitting procedure under taken by the signal comparison module 36 to compare an obtained breathing signal with a breathing model stored in the breathing model store 34 to identify abnormal breathing will now be described in detail with reference to FIG. 7.

Figure 7:
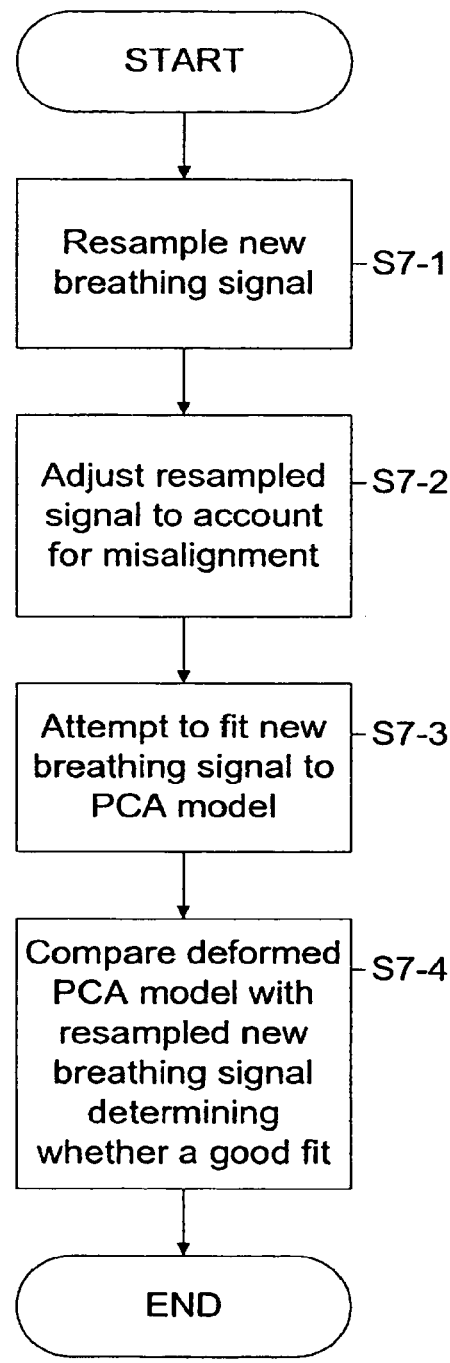
FIG. 7 is a flow diagram of the processing involved in comparing a breathing signal with a stored breathing model.

Turning to FIG. 7 which is a flow diagram of the processing involved in comparing a breathing signal with a stored breathing model, initially (S7-1) the captured breathing signal data is resampled in the same way as has previously been discussed in relation to the generation of a breathing model. This resampling is therefore such to generate a set of pairs of position and timing data representing the captured breathing signal where the number of pairs of data corresponds to the number of bins used to resample breathing signals when generating a breathing model.

The amplitude (position) measurements of resampled breathing signal are then adjusted (S7-2) in the same way that samples of sectioned breathing signal are adjusted to account for the differing extent of inhale and maximum exhale in different breathing cycle as has previously been described in step S5-2. This adjustment ensures that the subsequent fitting process can fit the stored breathing model to the breathing signal, without having to compensate for any misalignment in the amplitude range of both.

A set of weights $w_j$ for modelling the resampled adjusted breathing signal are then (S7-3) calculated as follows:

$$w_j = \frac{1}{\sqrt{\lambda_j}} P_j^T (X' - \bar{X})$$

where $\bar{X}$ is the sectioned breathing signal model's mean sectioned breathing signal, $P_j$ its eigenvectors and $\lambda_j$ its eigenvalues.

Once the stored breathing model has been used to calculate a representation of the new breathing signal, the quality of the fit is assessed (S7-4) to determine whether the shape achieved is a plausible fit.

In this embodiment, a plausible fit is identified as one whose amplitude shape and period are very similar to those in the sectioned breathing signal model's training data. A plausible fit measure D is therefore calculated as the Mahalanobis distance between the fitted sectioned breathing signal model and the sectioned breathing signal model's mean. The weights $w_j$ that are calculated as part of the sectioned breathing signal model fitting process are therefore used to calculate D such that $$D = \sqrt{\sum_{j=1}^{T} (w_j)^2} \,.$$

This distance represents the deviation of the fitted model from the sample mean and is compared with a value $D_{max}$. $D_{max}$ is chosen based on a Chi-squared value $x^2_p(r)$ for the number of degrees of freedom r contained in the model (number of principal variations r=T) and the probability p represented by these degrees (percentage of the total variation captured by T principal variations). Therefore, $D_{max} = \sqrt{x_p^2(r)}$ and a plausible fit is one that satisfies $D \leq D_{max}$.

When detecting bad sectioned breathing signals based on a model built with good sectioned breathing signal data, a plausible fit assessment gives an indication of a sectioned breathing signal being good (like one in the model's training set) or bad (unlike one in the model's training set) than an accurate fit assessment. The degree to which a sectioned breathing signal is marked as bad can also be quantified by assessing how much greater D is from $D_{max}$. If the accuracy of fit is determined to be less than a threshold value, this indicates that the breathing cycle is abnormal and in the event that two successive breathing cycles are detected, treatment can be halted until normal breathing resumes.

Second Embodiment

A second embodiment of the present invention will now be described. In the first embodiment determination of the regularity of a breathing cycle the apparatus is described based upon a comparison of sectioned breathing signals acquired by the patient monitor system. An improved system will now be described which is able to detect both irregular breathing and patient movement. In addition, the system in accordance with this embodiment is not dependent upon the placement of a marker 22 on the surface of a patient 20.

The overall architecture of a patient monitoring system in accordance with this embodiment of the present invention is similar to the patient monitoring system of FIG. 1 except that no marker 22 on the patient 20 need be provided and the 3D position determination model 25 is modified so as to process images obtained by the stereoscopic camera 10 to generate a 3D wire mesh model of the surface of the patient as viewed by the camera 10. Suitable means for processing images of stereoscopic cameras to generate 3D wire mesh models of patients are described in detail in the applicant's prior pending US patent application U.S. Ser. No. 10/516,400 published as PCT application WO2004/004828, which is hereby incorporated by reference.

As in the first embodiment, the result of processing by the 3D position determination module 25 is stored in a signal cache 28 together with a time stamp. Thus in this way a series of 3D wire mesh surfaces and associated time stamp data is stored in the signal cache 28. When data for a number of normal breathing cycles has been stored, this data is then processed by a modified phase detection module 30 and model generation module 32 to generate a principal component analysis breathing model modelling the manner in which a patient's surface varies throughout a breathing cycle. This breathing model is then stored in the breathing model store 34.

Subsequently during a monitoring phase, images obtained by the stereoscopic camera 10 are processed by the 3D determination module 25 and 3D surface data and timing data are stored in the signal cache 28. The phase detection module 30 then identifies when data for a complete breathing cycle has been stored. The signal comparison module 36 then compares the obtained signal with the stored principal component analysis model and identifies when the model is unable to match the generated surface data. In doing so, the signal comparison module 36 also determines a required motion to bring a detected surface back into alignment with the stored model. If it is found that the stored breathing model is unable to model a current breathing cycle, this indicates that irregular breathing or patient movement has occurred. A signal to halt the treatment can then be sent to the treatment apparatus 16 and where movement has occurred suitable instructions to take remedial action can be determined and sent to the mechanical couch 18 to realign the patient 20 so that treatment can continue.

Figure 8:
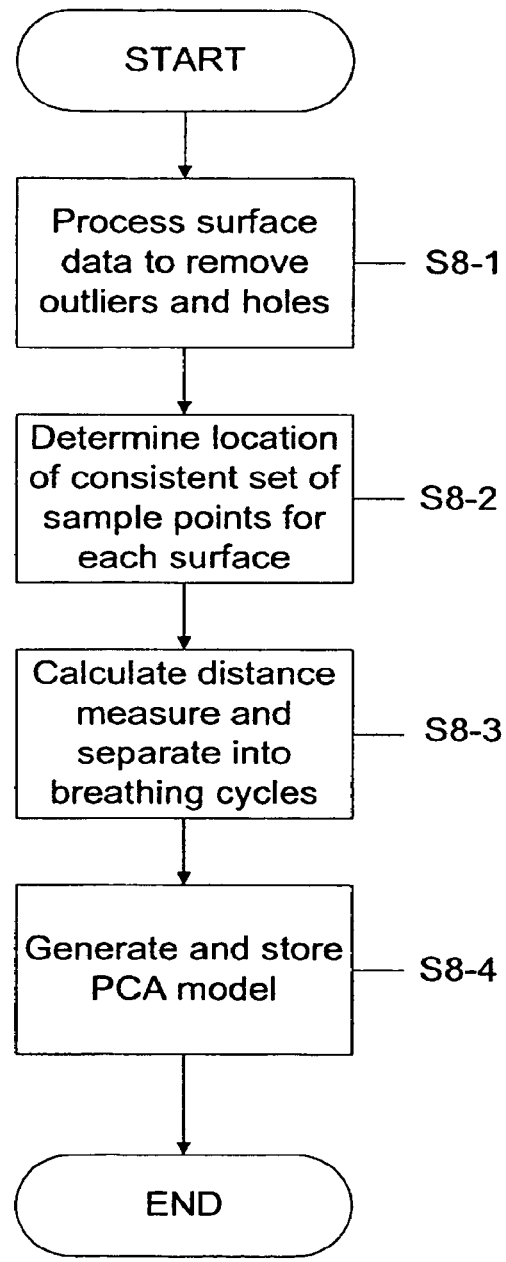
FIG. 8 is a flow diagram of the processing the processing undertaken by the patient monitor of a second embodiment to generate a breathing model for detecting irregular breathing and patient movement.
Figure 9:
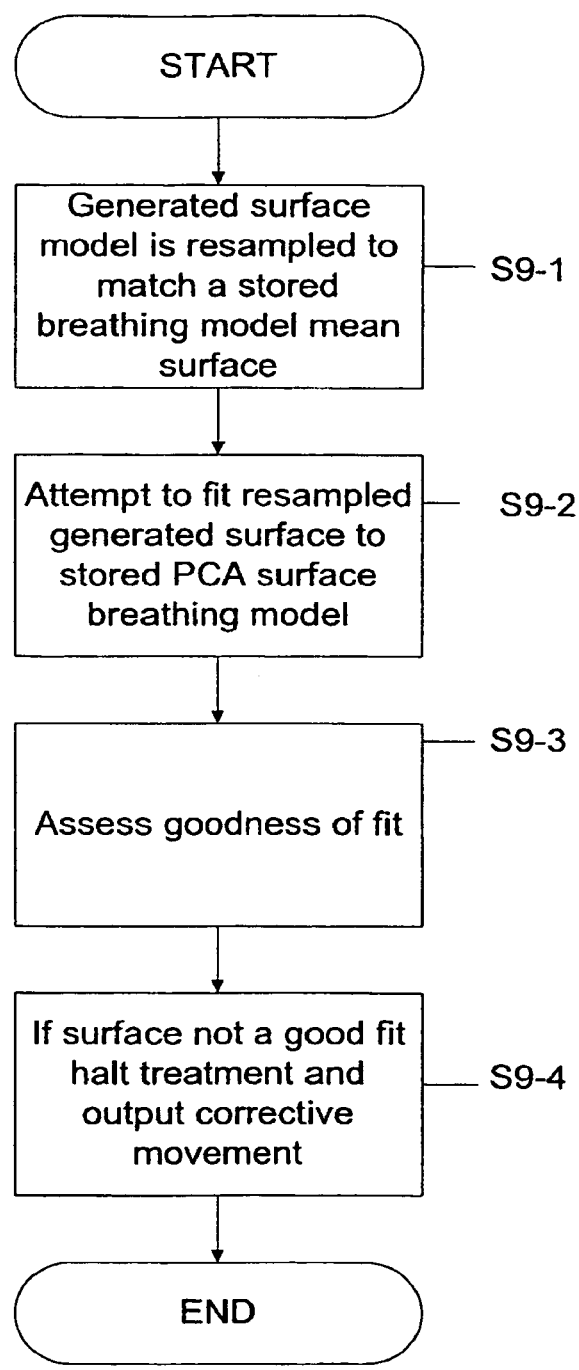
FIG. 9 is a flow diagram of the processing involved in comparing a breathing signal with a stored breathing model in the patient monitoring system of FIG. 8.

The processing undertaken by the phase detection module 30, the model generation module 32 and the signal comparison module 36 in this embodiment will now be described in detail with reference to FIGS. 8 and 9.

Generation of Surface Based Breathing Model

Due to the manner in which surface data is generated by processing images obtained by a stereoscopic camera 10, inconsistencies such as holes and outliers arise between successive surfaces. In order to overcome these inconsistencies a mesh deformation and hole filling approach is required to accommodate the varying surface characteristics including. To achieve this in this embodiment, the data representing surfaces is first (S8-1) processed using an energy minimisation process in which energy terms are defined for: (i) the point-to-point relationship between an initial reference surface being the surface for an initial pair of images obtained by the stereoscopic camera 10 and a surface generated for a subsequent pair of stereoscopic images, and (ii) the edge properties of the surface mesh of the initial reference surface. These energy terms are defined for corresponding vertices on both surfaces. The minimisation of these terms results in the transformation of reference vertices towards a subsequent surface such that the shape of the subsequent surface and the surface properties of the reference surface are preserved.

The data (point-to-point) energy $\varepsilon_{data}$ and smoothness (mesh) energy $\varepsilon_{smoothness}$ for corresponding vertices i on a reference and subsequent surface are defined as follows:

$$\varepsilon_{data}(i) = (X_n(i) - X_{n+1}(i))^2$$

$$\varepsilon_{smoothness}(i) = \frac{1}{E}\sum_{j=1}^{E}(X_n(i) - X_n(i))^2$$

where $X_n$ is the reference surface, $X_{n+1}$ is the projected surface for a subsequent surface, i is the vertex index for both reference and projected surfaces, and j is the vertex index for all E vertices connected to vertex i on the reference surface.

The combined energy ε for a vertex i that is then minimised in order to calculate a smooth projected surface that preserves the shape of a subsequent surface while maintaining the surface properties of the reference surface is defined as follows:

$$\varepsilon(i) = \alpha \varepsilon_{data}(i) + \beta \varepsilon_{smoothness}(i)$$

where ε is the weighted sum of $\varepsilon_{data}$ and $\varepsilon_{smoothness}$ with α, β∈R. α and β are used to control the deformation of a reference surface to match a subsequent surface, therefore resulting in a smooth projected surface with the shape of the subsequent surface but with the smooth mesh of the reference surface. Values for α and β are chosen as 1.0 and 0.2 for gated surfaces as these give a good trade off between shape preservation and surface smoothness.

When the combined energy is minimised for a given vertex i, a minimising translation t is calculated that minimises ε. This translation is calculated as follows:

$$t_{n+1}(i) = \frac{\alpha(X_{n+1}(i) - X_n(i)) + \frac{\beta}{E}\sum_{j=1}^{E}(X_n(j) - X_n(i))}{\alpha + \beta}$$

A smooth projected surface $Z_{n+1}$ will therefore have, a set of vertices i defined as follows:

$$Z_{n+1}(i) = X_n(i) + t_{n+1}(i)$$

A set of smooth projected surfaces Z were used as the resampled set of gated surfaces for a captured sequence and this resampled set is described as follows:

$$Z = \{X_1, Z_1 + t_2, Z_{n-1}t_n, \ldots, Z_{N-1}t_N\}$$

where an initial reference surface is the first in the resampled set i.e. $Z_1 = X_1$, and all subsequent resampled surfaces are calculated as the smooth surface projection of the previous resampled surface onto a generated subsequent surface i.e. $Z_n = Z_{n-1} + t_n$.

The phase detection module 30 then (S8-2) processes the data representing smoothed 3D wire mesh surfaces captured by the stereoscopic camera 10 to obtain for each smoothed surface data identifying the location of a number of points on the surface of the patient 20 where those points are tracked consistently from surface to surface.

In this embodiment, this is achieved by making an initial selection of points on the initial surface for the first pair of images obtained by the stereoscopic camera 10. These points are selected so that the points are spread out relatively evenly across a region of interest to be monitored corresponding to a patient's chest.

In order to identify the new positions corresponding to these points on the surface generated for the next pair of images obtained by the stereoscopic camera 10, each point is considered in turn. The intersection of a normal vector at a point with the surface generated for the next pair of images captured by the camera 1 is then determined. This is then repeated for all of the other points being monitored. The result of this processing is to identify the locations of the points being monitored at the time represented by the new images. This can then be repeated for each successive surface model stored in the signal cache.

Thus at this stage, the computer 14 will have stored for each of the surfaces generated by the 3D position data, a set of data $\{t_i, x_{i,1}, \ldots, x_{i,n}\}$ where $t_i$ indicates the timing associated with an image i captured by the stereoscopic camera 10 and $x_{i,1} \ldots, x_{i,n}$ indicate the 3D positions of points 1 . . . n on the surface of a patient at the time $t_i$.

The phase detection module 30 then (S8-3) utilises this data to derive a breathing signal which enables each set of data to be associated with a particular breathing cycle.

In order to do this, in this embodiment, the phase detection module 30 calculates a distance measure indicating the distance between each of the monitored points for which data is stored for a particular pair of images relative to the corresponding positions of those points in the surface for the initial pair of images. In this embodiment, this is achieved by calculating a distance measure:

$$d = \frac{1}{U}\sum_{i=1}^{U} r(i)$$

where r(i) is a signed distance between corresponding surfaces $X_n$ and $X_{n+1}$ i.e. $r(i) = |X_{n+1}(i) - X_n(i)|_{sgn}$, and all r(i) are ordered such that $|r(n)| \le |r(n+1)| \cdot X_n$ and $X_{n+1}$ have a total M vertices indexed by I but U vertices are chosen such that $U \le M \cdot X_n$ is a reference surface that is projected onto a subsequent surface to give a corresponding surface $X_{n+1}$.

The distance measure between the initial surface and all subsequent surfaces is then used to form a breathing signal which is then used to divide the stored data into data for a number of different breathing cycles in the same way as has previously been described in relation to the first embodiment.

Having divided the sets of data $\{t_i, x_{i,1}, \ldots, x_{i,n}\}$ into groups of data each associated with a different breathing cycle, the model generation module 32 then proceeds (S8-4) to generate a principal component analysis model using the data in a similar way to the generation of a principal component analysis model in the first embodiment.

More specifically a sample mean surface $\overline{Z}$ is calculated by summing the position data for the positions being tracked and dividing these sums by the sample size. This is expressed as:

$$\overline{Z} = \frac{1}{N}\sum_{n=1}^{N} Z_n$$

where N is the sample size and all $Z_n$ and $\overline{Z}$ are vectors of the form $\{x_{1,1}, \ldots, x_{i,n}\}$ The sample covariance matrix W is then calculated using $Z_n$ and $\overline{Z}$ prior to using principal component analysis to calculate principal or significant variations in surface shape that are present in the sample surfaces.

W is therefore calculated as: $W = (Z - \overline{Z})^T (Z - \overline{Z})$

The Eckart-Young Theorem is then used to ensure that suitable eigenvalues and eigenvectors are calculated from W A surface based principal component analysis breathing model for a given sample is then defined by the sample mean $\overline{Z}$ and the principal variations P(j) and λ(j) calculated using principal component analysis. This principal component analysis model defines a linear generative model where surfaces Y can be generated as:

$$Y = \overline{Z} + \sum_{j=1}^{T} w(j)\sqrt{\lambda(j)}\, P(j)$$

where all w(j) are weights used to vary the contributions of the different principal variations, and T is the number of principal variations used in the model. The weights w(j) are normally given a value of ±2 when individual principal variations j are displayed, while T is chosen as the number of variations that capture 90-100% of the sample variance, as calculated from the ordered λ(j).

Comparison of Live Data with Surface Based Breathing Model

After a surface based principal component analysis breathing model has been stored in the breathing model store 34, newly captured surface data is then matched with the stored model to identify abnormal breathing and/or patient movement as will now be described with reference to FIG. 9 which is a flow diagram of the processing involved in comparing a breathing signal with a stored breathing model.

Initially (S9-1), newly captured surface data is resampled to match configuration (surface topology and vertex count) of a surface model's mean surface. This is necessary in order to fit the surface model to the captured surface as it allows calculations to be made to determine the correct weights to use when fitting the model to the new surface.

In this embodiment, this resampling process is carried out using a two step projection and registration approach that ensures the resulting resampled surface accurately matches the captured surface.

First, the stored surface breathing model's mean surface is projected to a captured surface in order to establish an initial correspondence between both surfaces. The mean surface and projected surface are then registered using a Generalised Procrustes approach resulting in the mean surface being positioned closer to the captured surface. The mean surface is then projected to the captured surface and the resulting projection used as the resampled surface for the model fitting process. Then mean surface is restored to its original position prior to the model fitting.

Once the resampled captured surface has been established to match the surface model's mean, an accurate model is calculated (S9-2) using the model's linear generative model. This results in the determination of a set of weights $w_j$ being calculated for matching the new surface Z' to the model where the weights $w_j$ are as follows:

$$w(j) = \frac{1}{\sqrt{\lambda(j)}} P^T(j)(Z' - \overline{Z})$$

where $\overline{Z}$ is the gated surface model's mean surface, P(j) its eigenvectors and λ(j) its eigenvalues.

Once the principal component surface model had been fit to a captured surface, the quality of the fit is assessed (S9-3) to determine whether the shape achieved was an accurate fit, or a plausible fit.

In this embodiment an accurate fit is identified as one whose position and shape are very similar to a captured gated surface. A distance measure c between the fitted model and the resampled gated surface is therefore calculated to determine the accuracy of a fitted model. E is calculated as the mean distance between the vertices of the fitted model and captured surface i.e. ε=|Z'−Y|. A threshold $\varepsilon_{max}$ defining a "good" fit such that $\varepsilon \le \varepsilon_{max}$ can be calculated by fitting the gated surface model to its training data, and selecting either $\varepsilon_{max} = \max_n(\varepsilon_n)$ or $$\varepsilon_{max} = \frac{1}{N} \sum_{n=1}^{N} \varepsilon_n,$$

where $\varepsilon_n = |Z_n - Y|$.

A plausible fit is identified as one whose position and shape is very similar to that observed in the gated surface model's training data. A plausible fit measure D is therefore calculated as the Mahalanobis distance between the fitted gated surface model and the model's mean. The weights $w_j$ that are calculated as part of the model fitting process are therefore used to calculate D such that $$D = \sqrt{\sum_{j=1}^{T} (w(j))^2}.$$

This distance represents the deviation of the fitted model from the sample mean and is compared with a value $D_{max}$. $D_{max}$ is chosen based on a Chi-squared value $X^2_p(r)$ for the number of degrees of freedom r contained in the model number of principal variations r=T) and the probability p represented by these degrees (percentage of the total variation captured by T principal variations). Therefore, $D_{max} = \sqrt{\chi_p^2(r)}$ and a plausible fit is one that satisfies $D \le D_{max}$.

When detecting normal and abnormal breathing using a surface based breathing model built with normal breathing data (captured surfaces of a normal breathing sequence), an accurate and plausible fit assessment gives a reasonable indication of whether a newly captured surface has a normal position and shape (like one in the model's training set) or abnormal position and shape (unlike one in the model's training set). The degree to which a captured surface is marked as abnormal can also be quantified by assessing how much greater ε is from ε or D is from $D_{max}$.

When comparing the accuracy of a fitted gated surface model, $\varepsilon_{max}$ is chosen as $\max_n(\varepsilon_n)$ as this gives a better indication of an "outlier" position and shape when newly captured surfaces are assessed. The plausibility assessment is carried out using the defined $D_{max}$ value taken from the Chi-squared distribution. It has been determined that preferably both accuracy and plausibility assessments are made as together they offer a concise means of determining whether a subject's captured position and shape is consistent with that observed during a period of normal breathing.

In the event that the surface differs from the model by more than a threshold value, this indicates that a good match to the sample data cannot be achieved. In this embodiment, if this is determined to occur the signal comparison module 36 sends (S9-4) a signal to the treatment apparatus 16 to halt treatment. Additionally, the signal comparison module 36 calculates the translation required to realign the captured surface data with the expected position of a surface as represented by the stored breathing model. If for a period of abnormal breathing this corrective translation is approximately consistent, this will indicate that the patient 20 has moved. An appropriate set of corrective instructions can then be sent to the mechanical couch 18 to realign the patient 20 in the correct position so that treatment can continue.

Third Embodiment

A third embodiment of the present invention will now be described. This embodiment involves an extension of the modelling approach described in the previous embodiment. In contrast to the previous embodiment where a single model of the motion of a surface during breathing is generated, in this embodiment, in addition to a global model for modelling the entire breathing cycle, a number of sub-models that capture variations in the position, size and shape of surfaces during distinct portions of the breathing cycles are generated. This approach increases the range of variation that can be determined from captured breathing signal data and hence is able to model normal breathing and enable movement to be detected more accurately.

In order to generate a breathing model, as in the previous embodiment 3D surface data and timing data is captured during a training phase. In this embodiment, in addition to generating a global model in the same way as have previously been described, the captured data is additionally subdivided into a number of distinct training samples. This partitioning of surface data is carried out by first extracting a breathing signal from the data and using this as the basis for dividing the data into subsets that characterise different aspects of the breathing cycle e.g. points of maximum inhale and exhale and regions between these points. Individual breathing phases are then identified and partitions defined by amplitude within each phase. Once the surface data for a patient has been partitioned into amplitude partitions, a statistical surface model is built for each partition in the same way as has previously been described.

When amplitude partitions are used, the minimum and maximum amplitude values of all breathing phases define the amplitude range of the sample and the data is then segmented into a number of amplitude bands spanning this range. Thus, for example, in a system based on two sub-models the amplitude range would be split in half and surfaces from all breathing phases are grouped according to the bands they lie in. In systems involving more sub-models, the amplitude range would be split into the required number of amplitude bands to group the surface data for a patient.

By dividing the data in this way, the generated sub-models capture variations in surface data for a patient that correspond to specific amplitude bands, for example regions of maximum exhale, gradual inhale or exhale, and maximum inhale, etc. This grouping localises non-rigid surface variations within amplitude ranges i.e. non-rigid variations occurring during maximum exhale, inhale and maximum inhale for example. Therefore, when detecting positional changes due to breathing, amplitude sub-models corresponding to surfaces in particular bands are able to match non-rigid movements caused by changes in surface size and shape, and indicate rigid movements as residuals within specific bands. This produces a more accurate result than when a global model is used alone as it avoids the need to attempt to model the non-rigid surface changes across the whole amplitude range with a smaller number of principal variations than would be available in a sub-model model. This has been confirmed by a comparison of global models and amplitude based sub-models of surface data for a patient captured from a breathing phantom and test subjects. In all cases, amplitude sub-models have been seen to factor out more non-rigid variations and thus provide a more accurate means of identifying rigid surface shifts not caused by normal breathing.

When subsequently monitoring a patient's breathing the model generated using the complete set of captured surface data is then used to model the motion of the surface throughout the entire breathing cycle, whereas the separate models based on captured data for each of the partitions is used to model variations that are specific to their respective partitions when the measured amplitude is in the bounds associated with those partitions. As in the previous embodiment, if during monitoring a captured surface cannot be modelled, this will indicate that either abnormal breathing or patient movement has occurred with the comparison of a current surface occurring for the relevant portions of the breathing cycle each model represents.

Fourth Embodiment

A further embodiment will now be described in which multiple sub-models are combined to form a global model for modelling the entire breathing cycle.

As has been previously described, a surface based principal component analysis breathing model for a given sample having a sample mean $\bar{Z}$, principal variations $P(j)$ and eigenvalues $\lambda(j)$ defines a linear generative model where surfaces Y can be generated as:

$$Y = \bar{Z} + \sum_{j=1}^{T} w(j)\sqrt{\lambda(j)} P(j)$$

where all $w(j)$ are weights used to vary the contributions of the different principal variations, and T is the number of principal variations used in the model.

Where training data is divided into E groups each associated with different potions of the breathing cycle and E sub-models are generated, a surface model based on the multiple sub-models is defined by the linear generative model equation below:

$$Y = \sum_{k=1}^{E} a_k \left( \bar{Z}_k + \sum_{j=1}^{T_k} w_k(j)\sqrt{\lambda_k(j)} P_k(j) \right)$$

where Y is a model generated surface, $a_k$ are sub-model weights defining the strength of each sub-model k such that $0 \leq a_k \leq 1$ and $$\sum_{k=1}^{E} a_k = 1,$$

and $\bar{Z}_k$, $w_k(j)$, $\lambda_k(j)$ and $P_k(j)$ are the mean surface, mode weights, eigenvalues and eigenvectors specific to each sub-model k with $T_k$ principal variations.

In the general case, the sub-model weights $a_k$ of a model based on multiple sub-models may be set based on the membership of data within each sub-model as defined below:

$$a_k = \frac{1}{N} \sum_{i=1}^{N} f_k(Z_n)$$

where $f_k$ is a membership function which has value 1 if a smooth projected surface $Z_n$ as previously defined is part of sub-model k i.e. is positioned closest to the sub-model's mean surface $\overline{Z}_k$ and 0 otherwise. $f_k$ can therefore be defined as follows:

$$f_k(Z_n) = \begin{cases} 1: & |Z_n - \overline{Z}_k| < |Z_n - \overline{Z}_l| \forall\, l \neq k,\, l, k = 1, \ldots, E \\ 0: & \text{otherwise} \end{cases}$$

When this global model, based on multiple sub-models, is used to fit to new data the sub-model weights can be selected in such a manner as to favour a particular sub-model when it is more appropriate i.e. when it could produce a better fit to a captured surface.

In this embodiment, this is achieved by initially calculating a surface fit for each sub-model as follows:

$$Y_k = \overline{Z}_k + \sum_{j=1}^{T_k} w_k(j)\sqrt{\lambda_k(j)}\, P_k(j)$$

where sub-model mode coefficients $w_k(j)$ for a surface $Z'$ being fitted to are calculated as follows:

$$w_k(j) = \frac{1}{\sqrt{\lambda(j)}} P_k(j)^T (Z' - \overline{Z})$$

Suitable sub-model weights can then be calculated in a number of different ways to bias the model to the most appropriate sub-model.

One approach to achieve this would be to select the nearest sub-model using the membership function $f_k$ previously above so that $a_k = f_k(Z')$ Alternatively, the sub-model weights in other embodiments might be chosen based on their distance from all sub-model means $\overline{Z}_k$ such as by setting the weights as follows:

$$a_k = 1 - \left( \frac{|Z' - \overline{Z}_k|}{\sum_{k=1}^{E} |Z' - \overline{Z}_k|} \right)$$

Another alternative would be to choose the best fitting sub-model using a best fit function $g_k$ as defined below:

$$a_k = g_k(Z')$$

where the function $g_k$ is defined based on a most accurate model fit as follows:

$$g_k(Z') = \begin{cases} 1: & |Z' - Y_k| < |Z' - Y_l| \forall\, l \neq k,\, l, k = 1, \ldots, E \\ 0: & \text{otherwise} \end{cases}$$

or where $g_k$ is defined based on a most plausible model fit as follows:

$$g_k(Z') = \begin{cases} 1: & D_k < D_l \forall\, l \neq k,\, l, k = 1, \ldots, E \\ 0: & \text{otherwise} \end{cases}$$

Finally the fitted model Y is calculated as defined with:

$$Y = \sum_{k=1}^{E} a_k Y_k$$

As in the previous embodiments, detection of normal and abnormal breathing and movement can then be achieved in a similar way to the above described second embodiment where a calculated model fit is measured against a captured surface, and the resulting measure compared against a preset threshold to determine whether the model fit is sufficiently accurate or plausible to indicate normal behaviour.

FURTHER MODIFICATIONS AND AMENDMENTS

Although in the above described second embodiment, the patient monitoring system has been described waiting until surface data for a complete breathing cycle has been obtained and processed before identifying irregular breathing, it will be appreciated that patient movement can be detected without waiting for data for a complete breathing cycle to be captured. In such a system, a surface based breathing model could be generated using captured surface data in the absence of timing data. A model generated using such an approach would then model the variation in the shape of a patient surface as the patient breathes. Instantaneous surface data could then be compared with the stored model and if a newly captured surface could not be represented by the model, this would indicate patient movement. If the processing of a number of surfaces identified that a patient had moved, appropriate corrective action could then be taken in the manner described above.

In the first embodiment a system is described which monitors the variation of the motion of a single point on the surface of a patient with time. In contrast, in the second embodiment, a system has been described which matches surface data to a model of the manner in which the surface of a patient varies during normal breathing. Essentially, this second embodiment is equivalent to monitoring the movement of a plurality of different points on the patient's surface over time.

Thus in the case of the first embodiment data of the form $\{t,x\}$ is captured for each image frame whereas in the case of the second embodiment data of the form $\{t, x_1 \ldots x_n\}$ is captured where the system monitors the variation of n points on the surface of a patient. In a further embodiment, instead of considering just the positions of points on the surface of a patient, the motion and velocity of points being monitored could be modelled. In such a system, consecutive images could be processed to determine data of the form $\{v_1 \ldots v_n\}$ where $v_1 \ldots v_n$ are vectors indicative of the position and velocity of points on the surface of a patient being monitored. Such a system would enable both patient movement and abnormal breathing to be detected without waiting for a breathing cycle to be completed.

Although in the first embodiment, a system involving the placement of a marker 22 on the surface of a patient 20 has been described, it will be appreciated that the use of such a marker 22 merely simplifies the tracking of the motion of a point on the surface of a patient 20 and that a system such as that described in the second embodiment could be utilised to track the movement of a single point on the surface of a patient in the absence of such a marker 22.

It will also be appreciated that in other embodiments, rather than tracking the motion of points on the surface of a patient 20 using a stereoscopic camera other means could be used to obtain a breathing signal. Thus for example a marker 22 outputting a radio signal could be utilised and tracked. Alternatively a flow meter could be used to obtain a direct measurement of the through put of air into a patient's lungs and a breathing model generated using the obtained data.

Although in the first embodiment a single plausibility measure has been described to determine whether data for a breathing cycle can be modelled using a stored breathing model, it will be appreciated that other measurements of the extent that captured data can be modelled could be used.

Thus for example in order to identify whether a captured breathing cycle has an amplitude similar to those represented by a stored model, a distance measure e between the fitted model and the resampled and registered new sectioned breathing signal could be calculated to determine the accuracy of a fitted model. The mean distance E between sectioned breathing signal amplitudes and periods of the fitted model and new sectioned breathing signal i.e. $\varepsilon = |X'-Y|$ could then be determined and the result compared with a threshold t defining a "good" fit such that $\varepsilon \le t$ selecting either $$t = max_i(\varepsilon_i) \text{ or } t = \frac{1}{N}\sum_{i=1}^{N} \varepsilon_i.$$

Although in the above described embodiments, systems have been described in which treatment apparatus is deactivated when irregular breathing is detected, it will be appreciated that in other systems or embodiments, other actions could be undertaken. Thus for example in the case of a CT scanner, rather than deactivating a scanner, scans obtained whilst abnormal breathing was occurring could merely be labelled as such and a subsequent 4D model of the movement a patient's internal organs during a breathing cycle could then be generated using only scans obtained during normal breathing.

The third and fourth embodiments describe system in which multiple sub-models are generated by dividing training data based on an amplitude measurement. It will be appreciated that other ways could be used to divide data so that multiple sub-models could be generated. Thus, for example, instead of grouping data by amplitude, the data could be divided by associating surface data with different periods within a breathing cycle, where the period partitions were spread across the different parts of a breathing cycle between the start and end of a breathing phase i.e. points of maximum exhale and inhale. Sub-models could then be generated that captured the variation in position, size and shape of surface data for a patient occurring in those partitions e.g. for regions of inhale and exhale and others in between.

Although the use of sub-models has been described as providing a means for identifying abnormal breathing or patient movement, a surface model based on multiple sub-models can also be used to detect breathing phases where specific sub-models are highlighted as being the 'nearest' or providing the 'best fit' to a captured surface. Amplitude based sub-models would indicate when a surface was in a particular amplitude band e.g. in a region of maximum exhale, inhale/exhale, or maximum inhale. Period based sub-models would indicate when a surface was in a particular stage of the breathing phase e.g. start of inhale, end of inhale, start of exhale and end of exhale. Thus, if a phase marker is required to indicate entry into a particular amplitude range or stage of breathing, amplitude or period based sub-models could provide that function.

Although in the third and fourth embodiments systems, have been described which involve the generation of sub-models of surfaces, sub-models can also be implemented for 1D breathing signals by applying the same principles used for surface sub-models. 1D breathing signal data can be partitioned into amplitude and period partitions, and sub-models built for each partition. A 1D breathing signal model based on multiple sub-models would therefore consist of a number of individual sub-models and a global model. The fitting of the 1D breathing signal model based on multiple sub-models would be carried out again following the same procedures as described for surface sub-models but with 1D signals instead. Amplitude sub-models for 1D breathing signal data would model the range of amplitude values in each sub-model while period sub-models would model the range of amplitudes in certain stages of the breathing phase. Both types of model based on multiple sub-models could thus be used for breathing phase detection as they would both indicate amplitude ranges or phase stages that may be useful phase markers e.g. points of maximum inhale and exhale.

A further alternative would be to utilise the breathing monitor in the absence of any treatment apparatus such as might occur during breathing training where a patient attempts to regulate their breathing as much as possible to assist with the reliable application of radio-therapy. During breathing training a patient is typically shown a training signal that may be in the form of a bar graph which rises and falls in a manner representative of an idealised breathing signal and the patient then attempts to regulate their breathing accordingly. The above described system could then be used to generate a model of the regulated breathing and a patient could then be given feedback as to how well regulated the breathing was in terms of the variability of their breathing as modelled by the system. In such an embodiment or indeed any embodiment, the system could be connected to a display an output a warning when irregular breathing or movement was detected.

It will be appreciated that a breathing model could be created on one occasion during treatment, say for example during CT acquisition, and the same model for normal breathing reused on subsequent occasions. Alternatively, a new model could be generated from a period of normal breathing at the beginning of each treatment session.

Although in the above described embodiments, systems have been described which halt the application of radiation when abnormal breathing or patient movement is detected, it will be appreciated that embodiments of the system could also be used to select portions of a breathing cycle when radiation is to be applied. Thus for example in the case of the system of the second embodiment, the system could be arranged to irradiate a patient 20 only when a captured surface is no more than a threshold distance from a predefined reference surface.

Further it will be appreciated that once abnormal breathing had been detected, the abnormal breathing itself could be further classified before making any decision to halt treatment. Thus for example a system might be arranged to identify abnormal breathing and if the breathing merely represented rapid breathing, treatment might be continued whereas breathing classified as corresponding to coughing could cause the system to halt treatment.

Although in the above described embodiments, systems have been described in which principal component analysis models of breathing are generated, it will be appreciated that any suitable form of modelling which enabled the variability of movement corresponding to normal breathing could be used. Thus for instead of principal component analysis, an independent component analysis model could be generated for a breathing sample and abnormal breathing could then be identified by comparing data captured subsequently with the generated independent component analysis model.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

The invention claimed is:

1. A radio therapy device, comprising:
   a treatment apparatus for applying radiation to a patient, and
   a patient monitor, the patient monitor including:
   a 3D position determination module operable to determine measurements indicative of positions of at least part of a patient undergoing radiotherapy;
   a clock module operable to associate measurements indicative of positions of at least part of a patient determined by the 3D position determination module with timing data;
   a model generation module operable to (1) use obtained position and timing data for a plurality of breathing cycles obtained from the 3D position determination module and clock module to generate a component analysis model of the variation in position of at least part of a patient during the plurality of breathing cycles, and (2) model a representation of further position and timing data obtained from the 3D position determination module and clock module during a subsequent period of breathing using the component analysis model; and
   a comparison module operable to calculate a Mahalanobis distance between the modeled representation of the further position and timing data and a mean representation of the generated component analysis model, and compare the calculated Mahalanobis distance with a threshold value, and halt the application of radiation if the comparison between the calculated Mahalanobis distance and the threshold value indicated the breathing cycle is abnormal.

2. The radio therapy device of claim 1, further comprising:
   a phase detection module operable to process measurements indicative of positions of at least part of a patient obtained by the 3D position determination module and associate measurements with different breathing cycles, wherein the model generation module is operable to generate a component analysis model of the variation in position of the at least part of a patient during a breathing cycle using measurements determined by the 3D position determination module associated with different breathing cycles by the phase detection module.

3. The radio therapy device of claim 1, further comprising:
   a stereoscopic camera operable to obtain images of a patient to be monitored, wherein the 3D position determination module is operable to process images obtained by the stereoscopic camera to determine measurements indicative of positions of at least part of a patient being monitored.

* * * * *